(12) United States Patent
Nies (10) Patent No.: US 8,829,073 B2
(45) Date of Patent: Sep. 9, 2014

(54) IMPLANT MATERIAL BASED ON A POLYMER SYSTEM AND THE USE THEREOF

(75) Inventor: Berthold Nies, Fränkisch-Crumbach (DE)

(73) Assignee: InnoTERE GmbH, Radebeul (DE)

( * ) Notice: Subject to any disclaimer, the term of this patent is extended or adjusted under 35 U.S.C. 154(b) by 222 days.

(21) Appl. No.: 12/532,486

(22) PCT Filed: Mar. 27, 2008

(86) PCT No.: PCT/EP2008/053640
§ 371 (c)(1),
(2), (4) Date: Sep. 22, 2009

(87) PCT Pub. No.: WO2008/116905
PCT Pub. Date: Oct. 2, 2008

(65) Prior Publication Data
US 2011/0054392 A1 Mar. 3, 2011

(30) Foreign Application Priority Data
Mar. 27, 2007 (DE) .......................... 10 2007 015 698

(51) Int. Cl.
| | | |
|---|---|---|
| A61F 2/00 | (2006.01) | |
| A61K 6/08 | (2006.01) | |
| A61F 13/00 | (2006.01) | |
| A61M 37/00 | (2006.01) | |
| A61L 24/00 | (2006.01) | |
| A61L 27/44 | (2006.01) | |
| A61L 27/58 | (2006.01) | |
| A61L 27/56 | (2006.01) | |

(52) U.S. Cl.
CPC .......... *A61L 24/0042* (2013.01); *A61L 24/0036* (2013.01); *A61L 27/44* (2013.01); *A61L 27/58* (2013.01); *A61L 27/56* (2013.01); *A61L 24/0073* (2013.01)
USPC .............. 523/115; 523/116; 424/422; 604/82

(58) Field of Classification Search
CPC ............ A61L 24/0042; A61L 24/0073; A61L 2400/06; A61L 2430/02; A61L 2430/12
USPC ...................... 523/115, 116; 424/422; 604/82
See application file for complete search history.

(56) References Cited

U.S. PATENT DOCUMENTS

| | | | | |
|---|---|---|---|---|
| 4,093,576 | A * | 6/1978 | deWijn ........................ | 523/114 |
| 4,588,583 | A | 5/1986 | Pietsch et al. | |
| 5,650,108 | A * | 7/1997 | Nies et al. ..................... | 264/122 |
| 5,797,873 | A * | 8/1998 | Franz et al. ................... | 604/500 |
| 5,902,839 | A * | 5/1999 | Lautenschlager et al. .... | 523/115 |
| 6,160,033 | A * | 12/2000 | Nies ............................... | 523/116 |
| 6,409,972 | B1 * | 6/2002 | Chan ............................. | 422/131 |
| 6,593,394 | B1 | 7/2003 | Li et al. | |
| 2003/0130736 | A1 * | 7/2003 | Raab ........................... | 623/16.11 |
| 2004/0122126 | A1 | 6/2004 | Wu et al. | |
| 2006/0292199 | A1 | 12/2006 | Kuhn et al. | |
| 2007/0040151 | A1 * | 2/2007 | Utterodt et al. ........... | 252/182.13 |
| 2007/0043141 | A1 | 2/2007 | Wu et al. | |
| 2008/0039586 | A1 | 2/2008 | Hasenwinkel et al. | |
| 2008/0194729 | A1 | 8/2008 | Nies | |
| 2009/0105366 | A1 | 4/2009 | Vogt et al. | |
| 2010/0272649 | A1 * | 10/2010 | Nies et al. ..................... | 424/9.4 |

FOREIGN PATENT DOCUMENTS

| | | |
|---|---|---|
| DE | 32 45 956 A1 | 6/1984 |
| DE | 10 2004 049 121 A1 | 4/2006 |
| DE | 10 2005 023 094 A1 | 11/2006 |
| EP | 2052748 A2 | 4/2009 |
| WO | 98/24398 A | 6/1998 |
| WO | 2004/071543 A1 | 8/2004 |
| WO | WO 2005009481 A2 * | 2/2005 |
| WO | WO 2007007065 A2 * | 1/2007 |

OTHER PUBLICATIONS

Sarda et al., J. Biomed. Mater. Res, 2003, 65A, 215-221.*
The Free Dictionary, obtained online at http://www.thefreedictionary.com/formulation, downloaded on Apr. 20, 2012.*
Larraz E. et al.: Design and Properties of Novel Self-Curing Acrylic Formulations for Application in Intervertebral Disks Restoration; Biomacromolecules 2005, 6, 2058-2066.
Espigares I. et al.: New partially degradable and bioactive acrylic bone cements based on starch blends and ceramic fillers; Biomaterials 23 (2002) 1883-1895.
Kühn K.-D.: Bone Cements; Springer-Verlag Berlin Heidelberg New York, 2000, ISBN 3-540-67207-9; pp. 22-23 and Foreword.

(Continued)

*Primary Examiner* — Abigail Fisher
(74) *Attorney, Agent, or Firm* — Gudrun E. Huckett (57) ABSTRACT

An implant material on the basis of a polymer system has a first component and a second component that react with one another when mixed to form a polymer-based solid. The first component is a paste that contains at least one biocompatible polymer powder and a starter component for initiating a polymerization reaction upon mixing, wherein the paste has a carrier liquid, wherein under normal conditions in the carrier liquid the at least one biocompatible polymer powder does not dissolve or significantly swell and the starter component remains stable until mixing with the second component of the polymer system. The second component of the polymer system contains at least one reactive organic liquid or a solution or a suspension of a reactive organic liquid and of a polymer.

21 Claims, 1 Drawing Sheet

(56) References Cited

OTHER PUBLICATIONS

Gilbert et al.: A theoretical and experimental analysis of polymerization shrinkage of bone cement: A potential major source of porosity; J. Biomed. Mater. Res. 52, 210-218, 2000; cited in specification—p. 5, 2nd paragraph.

Boger A et al.: Properties of an injectable low modulus PMMA bone cement for vertebroplasty; European Cells and and Materials, vol. 10 Suppl 1, 2005 (p. 17); cited in specification—p. 6, 3rd paragraph.

* cited by examiner

IMPLANT MATERIAL BASED ON A POLYMER SYSTEM AND THE USE THEREOF

BACKGROUND OF THE INVENTION

The invention concerns an implant material based on a polymer system of at least two components and its use as a bone cement, bone adhesive, bone replacement material or active ingredient carrier.

Polymer-based bone cements are clinically used primarily for attachment of joint implants. They have been established for approximately 50 years in clinical practice and today are used worldwide in approximately 5 million cases. The chemical composition of the bone cements has practically remained unchanged during this time. It is comprised substantially of a powder component that contains one or several polymers, primarily comprised of acrylates, methacrylates, and styrene, or copolymers of these monomers or mixtures of the corresponding homopolymers and/or copolymers (referred to summarily as PMMA). Further components of the powder component are in general an x-ray contrast agent and a radical starter. As an x-ray contrast agent preferably barium sulfate or zirconium dioxide are used. As a radical starter in all commercially available bone cements dibenzoyl peroxide (BPO) is used. The second bone cement component is a reactive organic liquid that is quite predominantly comprised of the monomer methyl acrylate (MMA) and, in rare cases, also contains other esters of acrylic acid or methacrylic acid. Further components are a co-starter (also referred to as activator or co-initiator) and a stabilizer or inhibitor. As a co-starter in almost all commercial bone cements dimethyl-p-toluidine (DMPT) is used, very rarely another tertiary amine. As inhibitor primarily hydroquinone or one of its derivatives is employed.

In addition, bone cements can also contain further substances (antibiotics, coloring agents) that in the present context will however initially not be considered.

When in a conventional bone cement powder and liquid are mixed with one another, the initiator (BPO) and co-starter (DMPT) react with one another under formation of radicals that, in turn, attack the double bonds of the monomer molecules and trigger a polymerization (chain) reaction until the predominant portion of the monomer has reacted to polymer chains. Parallel to this, the monomer solubilizes or dissolves a portion of the polymer which initially may lead to a fast increase of viscosity of the cement material and which causes an intimate connection of powder and polymerizing liquid. The complete curing reaction from the mixture to the full loading capacity is completed in conventional PMMA bone cement in approximately 10-30 minutes. PMMA bone cements, despite the long experience and the wide use, have a series of disadvantages:

Mixing: the cement powder is a mixture of very fine powders that, in turn, have very different properties (particle size, density differences of 1.18 for PMMA and 5.85 for $ZrO_2$) and therefore are difficult to be homogeneously mixed and therefore require corresponding manufacturing expenditure. Mixing of the cement powder with the monomer liquid also constitutes a problem because the viscosity of the liquid increases very quickly and then a homogenous mixing is made difficult. A substantially pore-free cement material is practically achieved only by using complex and expensive mixing systems.

Shrinkage: during the polymerization reaction the density upon passing from pure monomer to polymer increases by more than 20% and the volume decreases correspondingly. Since the bone cement largely contains already polymerized material (PMMA proportion), in this system the shrinkage is significantly lower and is indicated to be approximately 2-5% (Kühn, Bone Cements, Springer Verlag, 2000, ISBN 3-540-67207-9). Aside from the high polymerization heat, the shrinkage can be considered a significant clinically relevant disadvantage of conventional bone cements that limits the application possibilities with respect to important clinical indications. In case of required great layer thicknesses (as, for example, when replacing a prosthesis) the shrinkage can cause the formation of a distinct gap between cement and bone so that a physiological force transmission is no longer possible.

Polymerization heat: the polymerization reaction of MMA to PMMA is greatly exothermic. The obtained peak temperatures according to ISO 5833 are at approximately 80° C. and depend quite considerably on the quantity ratio of monomer to total cement weight and to a lesser degree on the polymerization kinetics. Clinically relevant is the high polymerization heat in particular for large quantities of cement to be applied when the surrounding tissue cannot remove fast enough the generated heat in order to avoid tissue necrosis.

Mechanics: for most of the applications customary today PMMA bone cement has satisfactory mechanical properties. For some new applications—in particular, vertebroplastics or generally stiffening of spongy bone—the high stiffness is however often considered a disadvantage. A reduced stiffness may provide clinical advantages in many fields of application, even the traditional ones.

Active ingredient release: the majority of bone cement applications is focused today in many countries on the antibiotics-containing versions for prophylaxis of foreign body-associated infections. In order to achieve satisfactory release, very high doses must be mixed into the cement of which the predominant part is released over a very long period of time in very low concentrations (or not at all). This fact is often linked with the development and spread of resistant bacteria strains. Obtaining satisfactory effective levels at much lower dosages that may be released completely over a shorter period of time is therefore desirable.

Tissue compatibility: PMMA is tissue-compatible to a satisfactory extent and fulfills the standardized requirements with respect to biocompatibility of implant materials. PMMA however is not integrated into the bone but is encapsulated by scar tissue. This has biochemical causes as well as structural reasons. Solid bone cement provides to the surrounding bone no possibility to grow into an external pore system and to thus achieve a secondary interlocking as is the case in modern uncemented permanent metal implants.

WO 2005/009481 A1 discloses a bone cement containing a surface-active agent and comprised of a liquid component and a solid component. The powder component is unchanged relative to conventional bone cement; only the liquid component contains in addition to the monomer a surface-active ingredient and an accelerator. Immediately before use the components are mixed. The goal of WO 2005/009481 A1 is to impart to a conventional bone cement an improved release of antibiotic agents.

WO 2004/071543 A1 discloses an injectable bone replacement mixture of a) a two-component powder liquid bone cement, b) a further component that is not miscible with the cement paste, and c) an x-ray contrast agent. After mixing the components a self-curing porous bone replacement material is said to be formed in which component b after curing can be washed out. The teaching of WO 2004/071543 A1 is limited to a conventional powder liquid system to which, only after mixing the conventional components has been done, an immiscible liquid for pore formation is added.

DE 32 45 956 A1 concerns a surgical material on the basis of liquid monomer and powdery polymer acrylic acid esters and/or methacrylic acid esters, catalysts, accelerators, and optionally additives, in which the liquid component is not an aqueous emulsion but a solution with special organic liquids that do not participate in the polymerization reaction and that lead to a reduced heat development upon mixture and incorporation of the surgical material.

U.S. Pat. No. 4,093,576 discloses a bone cement mixture of a polymer powder and a highly viscous water-soluble gel of more than 200,000 centipoise that is compatible therewith. Upon mixing these components a porous bone replacement material is produced.

The object of DE 10 2004 049 A1 is an antibiotic-containing or antibiotics-containing PMMA bone cement with a powder component and a liquid component. In this connection, as a result of the specific composition of the added antibiotics their release is said to be significantly increased.

Cement-type compositions that are comprised of two pastes and are offered in double chamber syringes and are combined and reacted by means of static mixers have been known primarily from dental practice for quite some time. A product derived therefrom (Cortoss of the Orthovita company) has been developed in recent years also for the field of orthopedics. The dental filling materials as well as the product Cortoss differ significantly from the conventional bone cements as a result of their proportion of glass-ceramic filler materials in the first paste. As a starter system BPO/DMPT is employed wherein DMPT is contained in the first paste and BPO is present in dissolved form in the second paste and is stable with regard to storage only by cooling. A satisfactory storage stability is ensured for this product only for continuous cooling and the mineral fillers that are added in high concentration have the tendency, despite the high viscosities, to form sediments. The implant material according to the present invention is significantly distinguished from the products such as Cortoss and dental filling materials in that the materials according to the present invention always contain a suspension of polymer powders in carrier liquids in which they are neither soluble nor swellable to a significant extent. Furthermore, there is a significant material differentiation in that the products such as Cortoss in both cement components contain as monomers primarily macromers with more than one double bond while the monomer liquid in the materials according to the present invention predominantly are comprised of the monovalent MMA and polymers dissolved therein.

In recent years publications in regard to two-paste PMMA cements have also been published in scientific literature which are based on conventional bone cements (Li et al., Bioactive and osteoporotic bone cement, U.S. Pat. No. 6,593, 394 B1: Gilbert J L, Hasenwinkel J M, Wixson R L, Lautenschlager E P, J. Biomed, Mater. Res. 2000 October 52(1):210-218). These cases concern exclusively highly viscous solutions of PMMA copolymers in MMA with high contents of mineral filler materials in which one paste contains the BPO and the other one the DMPT. These compositions have thus the same technological disadvantages as Cortoss with regard to storage stability and sedimentation. Also disadvantageous in this connection is the very high heat development during polymerization that is caused by the necessary high MMA contents for the paste preparation.

In the early '80s of the 20th century the company Beiersdorf developed a bone cement and introduced it into the market which bone cement contains in the powder component a conventional composition but as a monomer liquid contains an emulsion of approximately 10% water in MMA. The goal was primarily lowering of the polymerization temperature. With the exception of use of emulsifying agents and aqueous components in the overall formulation there are no principal commonalities with the composition according to the present invention.

Inspired by clinical problems in connection with demands on bone cements for vertebroplastics, in recent years a series of tests for blending bone cements with aqueous polymer solutions, in particular hyaluronic acid, have been performed in order to reduce the stiffness of the cements.

According to Boger A., Verrier S., Bohner M., Heini P., Schneider E.—Injizierbarer poröser Knochenzement für die Vertebroplastik mit physiologisch angepassten mechanischen Eigenschaften (Injectable porous bone cement for vertebroplastics with physiologically matched mechanical properties), Bern; DGU, 2005—conventional bone cements were first mixed and subsequently hyaluronic acid was admixed. This procedure leads in contrast to the method according to the invention to results that are hardly reproducible and causes dramatic strength losses already for relatively low quantities of hyaluronic acid. The fundamental reason for the unsatisfactory results is linked to the practically unachievable uniform dispersion of aqueous solutions in an already pre-mixed bone cement paste under conditions in the operating room and with means that are available therein. The obtained cement materials are correspondingly inhomogeneous so that this method is impractical for clinical use. The cited works are therefore in no way an anticipation of the actual invention since neither the concrete teaching is disclosed nor the obtained results are achieved.

As a whole, the aforementioned works shows that there is an acute interest in an improvement of conventional bone cements and that the solutions that have been presented in the past are still far removed from a satisfactory solution.

The present invention ties in with the weak points of conventional PMMA bone cements in that it follows a new approach for preparation and material composition of bone cements while it is still based on the established starting materials. In this way, implant materials, in particular for bone cements, for vertebroplastics and filling of bone defects in the context of prosthesis revision and for the augmentation of osteoporotic bones are to be provided but also materials for non-medical fields of applications are to be developed.

SUMMARY OF THE INVENTION

According to the present invention, the object is solved by an implant material on the basis of a polymer system of at least two components that upon mixing react with one another and form a polymer-based solid, wherein the first component of the polymer system is a paste that contains at least one biocompatible polymer powder and a starter component for initiating a polymerization reaction upon mixing, wherein the paste is formed with the aid of a carrier liquid, wherein under normal conditions in the carrier liquid the polymer powder does not dissolve or significantly swell and the starter component remains stable until mixing with the second component of the polymer system, and wherein the second component of the polymer system contains at least one reactive organic liquid or a solution or a suspension of a reactive organic liquid and a polymer. Further embodiments and applications of this implant material are contained in the dependent claims.

The implant material according to the present invention on the basis of a biocompatible polymer system is comprised of at least two components that upon being mixed with one another react with one another and form a polymer-based solid wherein at least the first component of the polymer system is a paste of at least one biocompatible polymer and a starter component or a starter for initiating a polymer reaction upon mixing.

According to the invention the first component of the polymer system is a storage-stable paste of at least one biocompatible polymer powder and a starter component or a starter and a carrier liquid wherein the carrier liquid is selected such that under normal conditions the polymer powder will not dissolve or swell significantly and the starter component remains stable up to the point of mixing the components of the polymer system.

The second component of the polymer system contains at least one reactive organic liquid or a solution or a suspension of a reactive organic liquid and a polymer.

According to the invention the first component of the polymer system is embodied as a paste wherein the composition of this paste preferably is rooted in the composition of the powder component of conventional bone cements, i.e., contains polymer powder and radical starter (preferably BPO) and optionally x-ray contrast agents and optionally active ingredients. These components are combined with the carrier liquid such that the polymer powder and the starter component do not dissolve in the carrier liquid but are suspended therein. The suspension in the inventive form is present as a paste. Pastes are by definition suspensions of solids in liquids with a high solid contents. Pastes are usually not flowable but easily deformable. In the context of this invention the term paste is used as a descriptive term because an exact limitation based on viscosities is not available. Accordingly, pastes are to be understood as semi-solid materials that approximately cover the ranges that are also conventional with respect to toothpaste. The term paste however is to be understood to serve solely for differentiating the first component of the polymer system from the powdery, granular or other solid materials.

The gist of the invention is the novel formulation of the powder component of bone cements that are composed substantially of conventional materials as they are disclosed e.g. in Kühn, Bone Cements, Springer Verlag, 2000. For this purpose, the conventional powder components, polymer powder, x-ray contrast agent (if contained) and starter components and optionally further additives are formulated as a paste or suspension in a carrier liquid in which these components (in particular the starter component) are stable under normal conditions. Normal conditions are defined as 25° C. and 101.3 kPa.

The biocompatible polymer powder of the first component of the polymer system is selected from homopolymers or copolymers of acrylic acid esters, methacrylic acid esters, styrene derivatives, vinyl derivatives or their mixtures.

The implant material according to the invention on the basis of a self-curing/cold curing polymer system is based in a preferred embodiment on commercially available bone cements and their product specifications in order to tie into the long-standing experiences with these materials. A comprehensive overview of this product group is disclosed in the monograph Bone Cement (Kühn, Springer Verlag, 2000, ISBN 3-540-67207-9). The technology according to the invention makes available for the first time the possibility to go beyond the boundaries of prior bone cements with respect to composition and the property spectrum that can be achieved by the powder/liquid systems.

The selection of suitable polymers is exclusively based on their compatibility with the monomers systems to be used in accordance with the invention. The compatibility of polymers with one another is greatly influenced and limited by their chemical structure. This fact impairs, on the one hand, the selection possibilities for development and production of polymer blends but, on the other hand, it is also used in a targeted fashion in order to influence by separation processes and targeted incorporation of inhomogeneities the mechanical properties, the breaking behavior, tribological properties or other surface properties. Even when in the present invention with respect to the preferred use of the materials as a bone cement polymer systems on the basis of homopolymers or copolymers of acrylic acid esters and/or methacrylic acid esters, styrene derivatives, vinyl derivatives and/or their mixtures are the primary focus, in this context expressly all polymers are suitable and claimed that can be solubilized or dissolved in the polymerizable monomers and macromers or that can be fixedly bonded in a matrix of polymerizable monomers or monomer solutions.

For producing the first component as a paste at least one polymer (powder) and one starter (that may already be contained in the polymer) are suspended in a carrier liquid. The carrier liquid is preferably water or an aqueous solution (however, as mentioned above, in principle all other liquids can be taken into consideration that neither serve as a solvent for the starter nor the polymer). With respect to the preferred application as a bone cement biocompatible liquids that are established as pharmaceutical adjuvants are particularly preferred, in particular in addition to water and aqueous solutions, glycerin, glycerin ester, propane diol, low-molecular PEG, PEG-PPG-copolymers, DMSO, methyl pyrrolidone, biocompatible oils, their mixtures with one another and with other substances.

As a starter component or starter preferably a peroxide, preferably BPO, is used. The use of BPO in conventional bone cements has been established practice for decades. In these cases the BPO is present in the powder component and is phlegmatized with water (in special cases, the BPO is polymerized into the polymer component which also effects phlegmatization). In phlegmatized form the BPO is storage-stable for an extended period of time—commercially available bone cements have a storage stability of up to 5 years.

In commercially available two-component paste systems (Cortoss or other filler materials) the BPO is present in one of the components in dissolved form. In this form, the BPO is not phlegmatized and decomposes spontaneously as a function of temperature. The stability of BPO limits therefore the storage stability of this product. For increasing the storage stability the corresponding products must therefore be cooled which is undesirable for reasons of logistics.

In the implant material according to the invention the starter component in the carrier liquid is present in undissolved form. When using peroxide, the peroxide is preferably BPO as in conventional bone cements, preferably phlegmatized with water. Therefore, there are no disadvantageous effects with respect to storage stability.

As a carrier liquid all biocompatible liquids are possible in which the starter component is stable and in which the polymer powder will not dissolve or will not swell significantly (<5%). Especially preferred are water and aqueous solutions, glycerin, glycerin esters, propane diol, low-molecular PEG, PEG-PPG copolymer, DMSO, methyl pyrrolidone, biocompatible oils, their mixtures with one another and with other substances. The carrier liquid can have mixed in various substances that have the function, on the one hand, to suspend the powder components effectively in the liquid and, on the other hand, to influence the biological, mechanical, and structural properties of the bone cement.

The second component of the polymer system contains at least one reactive organic liquid or a solution or a suspension of a reactive organic liquid and a polymer. The reactive organic liquid is selected in this connection from methyl methacrylate or homologue esters of methacrylic acid or their mixtures.

The second component of the polymer system according to the invention is less strongly modified relative to conventional bone cements. Modifications relate here substantially to measures for affecting the viscosity and the wetting behavior so that both components are matched to one another and can be mixed with one another easily in the desired way.

The goal of this adjustment may reside, on the one hand, in that both components can be homogeneously mixed with one another and, on the other hand, in that during mixing predetermined and controlled inhomogeneities will occur. In the first case, the—modified—monomer liquid and the carrier liquid of the paste or of the powder suspension can be mixed with one another so that a molecular distribution without formation of phase boundaries between the employed liquids will result. In this case, the type and manner of polymerization corresponds to a solvent polymerization in which the solvent after completion of polymerization either remains permanently in the cement material or is later on partially or completely released into the surrounding medium.

In the second and preferred case the first and second components of the polymer system (paste or powder suspension and—modified—monomer liquid) upon mixing form a physical mixture in the sense of an emulsion in which the carrier liquid of the paste and the monomer liquid form separate phases. These physical mixtures are favored by the use of suitable emulsifying agents/surface-active agents or their mixtures and, if required, are assisted by stabilizers and are stabilized at least for the duration of the mixing step up to the termination of the polymerization reaction. In this case, the type and manner of polymerization corresponds to a suspension or emulsion polymerization in which, after intimate mixing of the two components, the—modified—monomer liquid and components of the powder paste form the continuous phase, while the suspended phase is substantially formed of the carrier liquid of the original powder paste. The actual polymerization takes place in this case practically exclusively in the continuous phase. Both components can be matched to one another such that the suspended phase forms isolated droplets or liquid-filled pores in the polymerized continuous phase or that the suspended phase forms an interpenetrating network with the continuous phase, i.e., a substantially interconnected pore system communicating with the external medium.

Experiments have surprisingly shown that from the powder component of conventional bone cements (e.g. Palacos® of the companies Biomet-Merck or Heraus Medical), an aqueous polymer solution (e.g. carboxy methyl starch), and a suitable biocompatible surface-active agent (e.g. Tween® 80) storage-stable pastes can be produced. These pastes can be mixed excellently with a conventional monomer solution (e.g. MMA solution for Palacos® of the company Biomet-Merck or Heraus Medical) in which minimal quantities of PMMA-PMA copolymer (e.g. Degacryl® of the company Degussa) are dissolved, wherein upon complete mixing within a short period of time a macroscopic, homogenous emulsion is formed that also within a short period of time (<10 min.) spontaneously polymerizes and forms a solid porous cement material.

The predetermined selection whether during the course of the curing reaction a solid or porous structure is formed, can be achieved in particular by selection of the carrier liquid of the first component of the polymer system. When the carrier liquid of the first component is miscible with the monomer liquid of the second component of the polymer system, one obtains primarily a solid material while the use of a carrier liquid that is not miscible with the monomer liquid produces a porous solid. In differentiating both cases, the term of miscibility is important. For complete miscibility or chemical mixtures the mixed substances are present in molecular distribution, i.e., the mixtures are homogenous up to molecular range and there are no phase boundaries between the mixed substances. Examples are solutions of substances within one another. In the present case, this applies to propane diol as a carrier liquid that is miscible with the MMA monomer. The polymerization then forms a solid material that is almost pore-free. The introduced propane diol after polymerization is (molecularly) distributed in the polymer matrix.

When no or no complete miscibility of the substance is present, phase boundaries between the substances are formed in that the suspensions (solid in liquid) or emulsions (liquid in liquid) can form. In the present case this applies when the carrier liquid of the first component of the polymer system and the monomer liquid are not completely miscible with one another. The preferred case is the use of an aqueous solution as a carrier liquid of the first component of the polymer system and a PMMA copolymer solution in MMA as a second component of the polymer system. MMA is only slightly soluble in water and therefore upon mixing of the two components no homogenous chemical mixture can be formed. The surface tension of the two liquids and their polarity differences effect a separation that however can be controlled by use of suitable surface-active substances (surfactants). Mixing of the two components of the polymer system has in this case the result that the suspended polymer powder of the first component—because of the similar polarity—will combine with the MMA liquid and the BPO (also suspended in the first component) also passes into the MMA because of its excellent solubility in MMA. In the MMA phase the polymerization can then take place because now BPO and DMPT are both present in the same phase and can react with one another. The presence of the polymer powder and of the surface-active agents combined with the increased viscosity of both components prevents a complete coalescence of the two phases and leads to formation of a contiguous pore system in which the aqueous solution of the carrier liquid fills the pore system.

In this context the following items are particularly surprising:

Mixing of conventional bone cement powder, an aqueous polymer solution, and biocompatible surface-active agents provides a storage-stable paste with macroscopic homogeneity and excellent handling properties, e.g., very high solid contents can be adjusted while at the same time extrudability by means of commercially available syringes is maintained. Sedimentation of components of the powder component, in particular of zirconium dioxide, was not observed.

The paste can be easily mixed with a conventional monomer that is matched with regard to viscosity in a simple mixing cup or in a generally known double chamber syringe (in the present case of the company Mixpac®, Switzerland) so that a macroscopically homogeneous cement material results. Even without special measures for open mixing no macropores are introduced into the cement material as is the case regularly in powder/liquid mixtures.

In the mixture according to the invention the polymerization reaction of the formulation that is based on the formulation of conventional bone cement (Palacos®) is significantly faster than in the comparable formulation in powder/liquid mixtures.

Especially surprising is the broad spectrum of mixing ratios between both components of the formulation according to the invention within which cement reactions with promising properties will occur. In particular, the powder pastes can be mixed with very much smaller quantities of monomer liquid than can be achieved with the powder/liquid mixtures.

The exothermicity can be reduced significantly as a function of the monomer quantity.

Despite the microporous structures of the cured cement surprisingly high strengths can be achieved.

The micropores form depending on the adjustment of the cement formulation according to the present invention an interconnected pore system. This property could not be obtained up to now for any self-curing implant material that has an appreciable structural strength.

Characteristic for the present invention is the realization of a self-curing polymer system that is comprised of at least two components wherein a first component contains a dispersion or suspension of polymer in a carrier liquid and this carrier liquid cannot dissolve the polymer nor can it cause a significant swelling of the polymer in the carrier liquid. In this connection, as a carrier liquid practically all liquids can be considered in which polymers that are suitable for producing self-curing plastic systems are stable. A further characteristic and prerequisite is that the starter system is compatible with the carrier liquid. In this regard, the invention differs fundamentally from known two-paste systems that throughout contain either multi-valent cross-linkable macromers or solutions of polymers in low-molecular, usually mono-valent, monomers. Starter and co-starter or initiator each are dissolved in one of the separated pastes and are reacted upon mixing the pastes so that the polymerization is initiated. Usually, these two-paste systems also contain various non-reactive fillers.

Important components of the carrier liquid are substances that improve the dispersibility of the polymer. Of great importance are moreover substances that can be used for adjusting the viscosity of the carrier liquid. These include in particular polymers which are dissolvable in the carrier liquid and/or viscous liquids that are miscible with the carrier liquid. Moreover, substances are included that can modify as very fine dispersions the viscosity and rheology of liquids, as in particular highly dispersed silicates and phosphates. Especially preferred polymers for adjusting the viscosity or generally the consistency of the first paste are biocompatible water-soluble polymers such as soluble starch and starch derivatives, cellulose derivatives, collagen, gelatin, PEG or PEO (polyethylene oxide), PEG-PPG-copolymers, water soluble modified polyacrylates/polymethacrylates, PVP, PVA etc.

in particular in the case of water-based polymer pastes the addition of suitable surface-active substances is advantageous.

Further additives of the first component depend on the desired field of application and comprise in particular the x-ray contrast agents disclosed for bone cements, antibiotics, other active ingredients, coloring agents, and filler materials.

The second component is comprised in a simple case of the (bone cement) monomer as a reactive organic liquid, a co-starter or initiator and an inhibitor for preventing premature polymerization. The co-starter can optionally also be provided in the first component. Since in the context of the present invention any liquid suitable for polymerization is suitable as a reactive organic liquid, substances are also included that are already used presently in two-paste systems (e.g. dental filler materials), i.e., usually multi-valent macromers such as bis-GMA and (di-, tri-, . . . , poly-) ethylene glycol dimethacrylate, multi-branched PEG-n-(meth-)acrylates and analog acrylates and methacrylates and their mixtures. These macromers have already a relatively high viscosity or can be adjusted by targeted mixing of the macromers to the desired viscosity. Further adjusting possibilities result by mixing with inorganic and organic fillers as they are known from the technology of dental molding and filling materials. For the application as bone cements, as fillers in particular those with bioactive properties are suitable, i.e., in particular calcium and/or phosphate-containing compounds.

In view of the preferred use of the materials according to the invention as bone cement the second component contains preferably the low-molecular monomer methyl methacrylate (MMA). Since MMA has a very low viscosity, a preferred embodiment of the invention resides in that the second paste contains a polymer dissolved in MMA and, by means of the type and quantity of dissolved polymer, the viscosity of the second paste is adjusted to the desired values. Even though basically all polymers soluble in MMA are conceivable, those of the type of polyacrylic acid ester, poly methacrylic acid ester, polystyrene, and their copolymers are preferred. Especially preferred are the polymers, respectively, that in a two-paste system are substantially the same as (or identical to) the respective chemical composition of the dispersed polymers of the first paste and—if at all—differ only in regard to the copolymer contents and/or molecular weight.

The second component of the polymer system can also be present as a paste but also as a liquid (solution) with a viscosity of preferably <200 Pa*s.

According to a preferred embodiment of the invention, the starter—possible is also to provide starter and co-starter together—is also in a form in the carrier liquid in which it is stable. Typically, it is present as a dispersion in the carrier liquid or it is contained in the dispersed polymer. The radical starter BPO that is contained in all commercially available bone cements is employed in these two forms and the technology according to the invention in both cases can be realized in the same way. The stability of the radical starter—such as BPO—in aqueous dispersion is technologically a great advantage relative to known two-paste systems that work with dissolved BPO because BPO, like other conventional peroxides in dissolved form, has the tendency to spontaneously decompose and is therefore only storage-stable to a limited extent. Corresponding bone cements such as Cortoss® by Orthovita must therefore be stored with cooling in order to limit the premature decomposition of BPO. In the present invention, preferably an aqueous solution as a carrier liquid is employed and dispersed BPO is storage-stable therein to an unlimited extent. The same holds true also for other relevant peroxides.

According to an advantageous embodiment the components of the polymer system contain a starter system of a two-component radical starter with a starter component and a co-starter, polymerization accelerator or initiator as a second radical starter component. In this connection, the starter component is present in the first component of the polymer system in undissolved form and the second radical starter component is contained in the second component of the polymer system.

Preferably, the starter component is a peroxide and the second radical starter component is a tertiary amine. The respective components of the starter system are substantially stable and storable in the respective component of the polymer system at normal conditions until components are mixed.

Inasmuch as the polymer system requires for reaction a co-starter or initiator, the co-starter or initiator is present preferably in dissolved form in the second component but can also be a suspended or dissolved component of the first component inasmuch as both components of the starter system in the carrier liquid of the first component of the polymer system cannot react with one another because e.g. one or both components of the starter system are insoluble in the carrier liquid. As a co-starter tertiary amines are preferred as they are used currently in commercially available bone cements. Basically, all co-starters are however suitable in this context which are practical in medical and technical polymerizations systems. The selection of the starter system depends on the application purpose of the polymer system according to the invention.

The polymer system according to the invention contains the starter in finely divided form in the carrier liquid (wherein it can be present in freely dispersed form as well contained in the polymer or adsorbed to the polymer surface). Additionally, also the co-starter can already be contained in the carrier liquid inasmuch as it is ensured that both substances, e.g., because of lack of solubility in the carrier liquid, are stable in this environment and neither decompose prematurely nor react with one another. In the polymer system according to the invention both components and the starter components contained therein therefore are stable until they are mixed with one another. This holds true also for conventional two-paste polymer systems; however here only the reaction speed of the starter is lowered in order to achieve by a precisely matched ratio of starter to inhibitor (in combination with storage under cooling) an acceptable storage capability for practical use. An important aspect of the present invention is therefore that the starter is dispersed in a carrier medium (carrier liquid of the first component) in which it is storage-stable to a satisfactory degree. Upon mixing first and second components a transfer of the starter from the first into the second component takes place with dissolving of the starter component. As soon as the starter is dissolved in the second component of the polymer systems, it reacts spontaneously with the co-starter (if required) and initiates the polymerization of the monomer or macromer. According to the present invention the employed starter is thus insoluble in the first component and soluble in the second component and mixing of both pastes leads to dissolving of the starter and co-starter in the same phase so that both substances can react with one another (if dissolving of the starter in the reactive monomer solution alone does not lead to a satisfactory reactivity).

The implant material according to the invention of two components can be formulated such that the carrier liquid of the first component and the monomer solution of the second component are partially or completely dissolvable in one another so that both liquids form solutions or mixtures in the chemical sense. This is, for example, the case when organic liquids such as propane diol are used as carrier liquid for the first paste and the monomer solution of the second paste is based on MMA. Advantages in this embodiment primarily are based on a different mechanical behavior because in this case a homogenous matrix is formed and no pore system. Another important aspect is present when the inventive implant material is to be used as an active ingredient carrier. In this case, by means of such a dense matrix that in regard to its density can be very well adjusted the active ingredient release can be matched to the requirements within wide ranges.

A particularly preferred embodiment of the invention resides in that the carrier liquid of the first component and the monomer solution of the second component in the chemical sense are not miscible and/or not soluble or only minimally soluble in one another and that therefore upon mixing of the components substantially a physical mixture with formation of at least two separate phases results. This situation is particularly present and in particular preferred when the carrier liquid of the first component is an aqueous solution and when the second component is based on a monomer solution wherein the employed monomers have a minimal solubility in water. The latter is particularly present when as a monomer MMA or other non-polar esters of acrylic acid or methacrylic acid (e.g. butyl methacrylate) or styrene or their mixtures are used. In this connection it is expressly underscored that the non-miscibility or minimal solubility is related only to the carrier liquid and the monomer liquids and that the substances that are dissolved in both liquids or in particular suspended therein can still dissolve in the other liquid, respectively.

The polymer system according to the present invention contains in general one or several substances that are present in suspended form in the respective carrier liquids and whose surface properties may counteract a stable dispersion. This is true, for example, for non-polar polymer powders that are suspended in aqueous solution or polar substances that are suspended in the monomer liquid. It is therefore an aspect of the invention that these dispersions by suitable surface-active substances are enhanced and stabilized. In the case of the application as a bone cement or generally as an implant material biocompatible surface-active agents are used for this purpose and in particular those that are approved and/or successful as pharmaceutical adjuvants.

Moreover, a preferred aspect of the present invention is the targeted addition of surface-active substances to one or both (or all) components of the polymer system according to the invention which in case of components whose liquids are not miscible in the chemical sense with one another or only have a minimal solubility in one another, assist in the formation of a physical mixture of the two pastes and stabilize this mixtures at least until polymerization has advanced to such an extent that no longer a significant or disadvantageous separation of the components can occur. As surface-active substances in principle all substances are to be taken into consideration that for the respective application of the polymer system according to the present invention are suitable and approved, in particular—in the case of use as implant material—all biocompatible surfactants that are currently also employed already in pharmaceuticals, cosmetics, foodstuffs or medical products and/or are approved for such applications. For technical applications the same holds true.

It is known in pharmaceutical technology and in cosmetics that in many cases the combination of several surfactants for obtaining the desired effect are required or that by combination of different surface-active agents effects can be achieved that cannot be realized with a single substance. It is therefore a preferred aspect of the present invention that at least one or all components of the polymer system contain at least one biocompatible surface-active agent that assists in the formation of a physical mixture of the components.

Preferred among the plurality of possible surfactant additives are primarily biocompatible anionic and non-ionic surface-active agents. On the one hand, these two groups in principle are considered to be better compatible and, on the other hand, they encompass almost any number of homologue derivatives with which a targeted adjustment of property spectra is possible. Especially preferred in case of implant materials are formulations in which at least one component contains a bio-compatible anionic surface-active agent that contains at least one carboxyl group, sulfate group or phosphate group because these surface-active agents at the same time may serve as crystallization seeds for bone minerals.

Also particularly preferred is the use of anionic surface-active agents of the type of soap, i.e., fatty acids and their alkali salts or alkaline earth salts. Among these, especially preferred is the use of oleic acid and its sodium, potassium, ammonium, calcium, zinc and magnesium salts.

Especially preferred are furthermore formulations that contain more than one surface-active agent wherein at least one of the surface-active agents is anionic and at least one second surface-active agent is non-ionic. In this context, also such surface-active substances are to be understood as a non-ionic surface-active agent that in the technological terminology are referred to as co-surfactants and, for example, comprise aliphatic alcohols. Especially preferred are those surface-active agent combinations which assist the components of the polymer system according to the invention to form (spontaneously) microemulsions upon mixing. Microemulsions have the great advantage that they can form spontaneously, have a reproducible structure, and are thermodynamically stable. Their formation therefore leads to a particularly homogenous matrix of the polymerized monomer solution.

According to a preferred embodiment of the invention at least one component of the polymer system contains at least one biocompatible non-ionic surface-active agent of the group of polyoxyethylene fatty alcohol ethers (Brij types), polyoxyethylene sorbitan fatty acid esters (Tween types), alkyl aryl polyether alcohols (Triton types), polyoxyethylene polyoxypropylene polymers (random or block; Pluronic types). According to a further preferred embodiment at least one component of the polymer system contains at least one biocompatible anionic surface-active agent of the group of fatty alcohol sulfates, fatty alcohol sulfonates, their ethoxylates, their respective alkali salts, the group of fatty alcohol phosphates (amphisol types), fatty alcohol phosphonates, their ethoxylates and/or their alkali salts.

According to a further embodiment of the invention the carrier liquid or the monomer solution contains water-soluble monomers or macromers that during or after polymerization of polymer system are also polymerized. These water-soluble monomers or macromers polymerize preferably at the boundary surface to the polymer matrix or directly in the aqueous solution. They generate thus in the aqueous phase a hydrogel that either is deposited on the polymer matrix or that fills the aqueous phase more or less homogeneously. In this way, composition, diffusion behavior, swelling behavior etc. of the aqueous phase can be affected additionally. Examples of suitable water-soluble monomers are methacrylic acid, HEMA, HPMA, HEMA phosphate, sulfopropyl methacrylate, their homologues, and their mixtures. Examples of water-soluble macromers are PEG-mono-methacrylate, PEG-di-methacrylate, branched PEG-n-methacrylates, their homologues and their mixtures. These listings have only exemplary character; comprised are all polymerizable water-soluble monomers whose polymerization may result in hydrogels.

The quality of the implant material according to the invention depends in special applications quite fundamentally on the fine adjustment of the two components. The embodiments show that with relatively simple polymer systems already very good results can be obtained. However, the requirements in regard to the polymer system depending on the field of application can be very different. As already mentioned above, it may be expedient to provide a polymer systems that form a pore system by phase separation or immiscibility of two phases. As a bone implant it can be desirable furthermore that such a pore system largely or completely is interconnected so that the surrounding bone can grow in. This object places great demands on the composition of the two components so that by means of viscosity, structural viscosity, surface-active substances, particle size of the suspended polymers, and auxiliary agents and polarity of liquids the formation of the pore system can be controlled. Methods and auxiliary substances for a targeted manipulation of the behavior of powder/liquid mixtures and emulsions are primarily known from pharmaceutical technology and cosmetics. In the present invention these technologies are used for the first time in order to realize a novel implant material. Especially claimed are therefore embodiments of the polymer systems according to the invention in which the respective components are adjusted with respect to their viscosity by polymers contained and dissolved therein or finely divided suspended organic, inorganic or organo-mineral components and by means of which mixing and separating behavior before and during polymerization can be affected. Such substances are, for example, water-soluble polymers such as soluble starch and starch derivatives, cellulose derivatives, collagen, gelatin, PEG, PEG-PPG copolymers, water-soluble modified polyacrylates/polymethacrylates, PVP, PVA etc. that may be present dissolved in the aqueous phase as well as dissolved in the organic phase (monomer) or suspended. For adjusting the viscosity of the organic phase all polymers are suitable that are soluble in the respective monomer solution and that are compatible with the polymer components. This holds true in particular for the respectively selected polymers of the first component which however may differ from the employed particulate polymers in particular with respect to molecular weight. These polymers can also be used directly as a solution in the monomer or as a particularly finely dispersed powder in the water-based first component so that these particularly finely dispersed particles in contact with the monomer solution will dissolve very quickly and effect a fast viscosity increase in the monomer solution. In addition to the dissolved or soluble substances, additives are conceivable that in both components or phases are insoluble and that primarily affect the structural viscosity of the components or stabilize the phase boundaries, such as finely divided silicates and phosphates that optionally can be modified additionally.

An important aspect of the present invention is the excellent miscibility and the minimally invasive administration of the two components of the polymer system. Tests have shown that for manual mixing, in particular however mixing in a two-chamber system and static mixers, the viscosity of the two components during mixing may not be too high and advantageously should further increase significantly only after the mixing step. The viscosity of the components of the polymer system (before mixing) is therefore advantageously at a value of <200 Pa*s. At higher viscosities a thorough mixing of the components is made more difficult or extrusion by a static mixer is impaired.

In particular in case of use of the polymer system according to the invention as bone implant materials microcrystalline, nanocrystalline or amorphous calcium phosphates are preferably used as mineral additives. They can have, on the one hand, the function, as mentioned above, to modify the viscosity of the pastes and/or to stabilize the phrase boundaries between the aqueous phase and the organic phase. Moreover, they can have additionally or primarily a biological function in that they increase the bioactivity of the implant material and advance growing of bone into an optionally present pore system.

The bioactivity of the polymer system according to the invention as an implant material for applications in the bone area is advanced particular preferred in that at least one of the components contains substances which after introduction of the material at an implant site enhance the mineralization of the surface of the implant material. Methods for bioactivation of bone cements are disclosed in DE 10 2005 023 094 A1.

A preferred variant resides in that the polymers suspended in the first component of the polymer system are comprised entirely or partially of copolymers that contain anionic groups or can dissociate or hydrolyze to form such groups.

Especially preferred are those copolymers that contain phosphate, carboxyl, sulfate, or silicate groups. Also particularly preferred are compositions that aside from such anionic copolymers contain calcium salts and/or buffer substances that have a high buffering capacity in the alkaline range. The calcium salts and the buffering substances may be contained in any of the components. Especially preferred are also compositions that contain anionic monomers in the second component of the polymer system and/or in which anionic copolymers are dissolved or suspended in the second component of the polymer system.

The method described in DE 10 2005 023 094 A1 is used in the present case for the first time on the implant material according to the invention and has in this case the special effect that the bone not only can grow in on the surface of the implanted bone cement but also can grow into a pore system that is being formed. It is therefore particularly preferred that the polymer systems according to the invention—inasmuch as they are to be used as bone implant material—contain substances e.g. ethylene glycol methacrylate phosphate or methacrylic acid that may serve a mineralization seeds for deposition of bone-analogue minerals. In addition to the mineralization seeds themselves at least one component may contain additives in particular soluble calcium salts and buffering substances that may advance mineralization. The buffering substances are able to adjust or keep in the direct vicinity of the implant material the pH value in the adjoining aqueous medium at a neutral to alkaline range, preferably pH 7.4 or above.

Advantageously, at least one component contains at least one biocompatible substance that under biological conditions and in particular under conditions as they are present in the bone serve as crystallization seeds for mineral depositions and/or advance the formation of such mineral depositions. In particular polymer substances are provided for this purpose with at least one carboxyl, sulfate and/or phosphate group or a siloxane group as a substituent.

The implant material according to the present invention and the method for producing bone implant materials comprised thereof enable a targeted influence on the components of the phases that are being formed. In particular, during the course of mixing of the two components and the subsequent polymerization two phases can be formed whose composition can be controlled in a targeted fashion. The water-based phase can be understood as a pore system within the continuous polymerized organic phase wherein, with appropriate selection of the composition of the polymer system and the processing parameters, the water-based phase can also form a continuum and thus form an interconnected pore system. For the biological behavior the composition of the water-based phase is of particular importance. In addition to the essential components of the aqueous solution that serves as a carrier liquid of the polymer suspension of the first component, it can contain various auxiliary agents and active ingredients which, on the one hand, affect the cell activity in the surrounding tissue and, on the other hand, can contain active ingredients that are to be released from this pore system into the surroundings of the implant material and whose release kinetics can be effectively controlled by means of the auxiliary agents contained in the aqueous phase. An important example in this connection is the combination of a large proportion of the conventional bone cements with antibiotics that, as mentioned above, are released only very slowly and in very minimal quantity from the cement matrix. In the case of the inventive polymer system, the antibiotics (and/or other suitable agents) can be added to one or both pastes depending on whether a quick or slow release is desired (as a result of the large surface area the release action in any case will be much faster than in all conventional bone cements). The predominantly relevant water-soluble active ingredients—such as antibiotics—are preferably added to the first water-based paste and after polymerization of the implant material are practically exclusively present in the aqueous solution that fills the pore system. When the pore system is substantially interconnected, the active ingredients can be released quickly by diffusion out of the pore system. In this way, the active ingredients can be added to the bone cement in much lower dosage in comparison to dosage used currently in conventional bone cements. In addition, the risk of developing resistance as a result of sub-inhibitory antibiotic concentrations is eliminated, which risk, in the case of conventional antibiotic-containing bone cements, has not yet been eliminated and represents a significant approval hurdle.

The release of the active ingredients can moreover be controlled in wide ranges in that by selection of suitable salts the solubility of the active ingredients can be affected, e.g., the solubility of cationic antibiotics that are primarily used in bone cements, such as amino glycosides (gentamycin, tobramycin) and glycopeptides (vancomycin), can be reduced significantly by lipophilic and amphiphilic anions and a prolonged release can be achieved in this way. A further very effective control of the release results by use of auxiliary agents in the aqueous phase that impair free diffusion of dissolved active ingredients, i.e. practically plug the pore system. These agents can be in particular the same auxiliary agents that as water-soluble polymers such as soluble starch and starch derivatives, cellulose derivatives, collagen, gelatin, PEG, PEG-PPG copolymers, water-soluble modified polyacrylates/polymethacrylates, PVP, PVA, etc., effect the viscosity of the aqueous phase but also particulate and optionally swellable substances such as starch derivatives, insoluble collagen, gelatin (insoluble) or mineral particles such as silicates or calcium phosphates that also can adsorb and release with delay optionally added active ingredients.

Especially preferred are components that form a pore system that is interconnected predominantly or completely. This provides decisive advantages for the biological behavior in that the surrounding tissue thus has the possibility to grow deeply into the pore system. Further advantages result in connection with the active ingredient release. In certain applications and in certain formulations—that are not limited to the use as implant materials—there result also biochemical or technological advantages. Biochemical advantages are provided inasmuch as an interconnected pore system can function in an elastic polymer matrix as an effective hydrodynamic system that reacts in a damping fashion in that the liquid is forced out of the pore system and flows back upon load relief. In comparison to materials available up to now, such a material can better mimic in the bone area primarily the biomechanical function of the spongy bone of the joint-near areas and of the spine.

The formation of a pore system in the implant material according to the invention occurs automatically when as a carrier liquid for the first component a substance is used which is not miscible with the monomer liquid. In many applications the minimization of porosity is desirable for mechanical reasons as is attempted also in conventional bone cements. Especially in the field of application of osteoporotic bone however also a reduced stiffness of bone cement is desirable for biomechanical reasons. For such applications formulations with an increased porosity are desired. Examinations have shown that in particular for higher porosities the compression strength of the samples is significantly reduced but is still at a level that in particular for filling osteoporotic bone is viewed to be particularly beneficial (see: Boger A., Verrier S., Bohner M., Heini P., Schneider E.—Injizierbarer poröser Knochenzement für die Vertebroplastik mit physiologisch angepassten mechanischen Eigenschaften (Injectable porous bone cement for vertebroplastics with physiologically matched mechanical properties), Bern; DGU, 2005). The examples show also that the goals mentioned in the cited work can be achieved with the implant material according to the invention in an excellent and reliable way. Preferred are therefore compositions of the implant material according to the invention that result in a porosity (i.e., they thus comprise immiscible combinations of carrier liquid and monomer liquid). Particularly preferred are compositions that result in a porosity of >10 percent by volume in the cured implant material and especially preferred are compositions that result in a porosity of >15 percent by volume.

The combination of implant materials according to the invention with pharmacologically active ingredients or other substances that serve an additional function has already been explained at various locations. At this point this claim will be summarized and particularly underscored because of its relevance for the present invention. Claimed are all active ingredients that are essential for the function of the polymer system according to the invention, that may assist in its intended application as a medical product or technical product or may expand its use to further fields of applications. The already mentioned and the following examples are not to be understood in any way as limiting.

For the use of the implant materials according to the invention as bone implant materials, the combination with substances that generally facilitate imaging diagnostics or make it possible at all is of particular importance. These substances include the classic x-ray contrast agent of bone cements ($BaSO_4$, $ZrO_2$) as well as often experimentally employed metal powders (Ta, W, Fe, Co or alloys of these elements). Furthermore, the combination with non-ionic x-ray contrast materials (usually organic iodine compounds) or the use of iodine-containing monomers or polymers is included as well as diagnostic active ingredients that are important for imaging methods other than x-ray (Tc, Gd).

Antimicrobial active ingredients have been established as an additive to bone cements for many years—their advantageous use or the advantages of the invention for the combination with active ingredients for the local application are already apparent from the discussions above. For the polymer system according to the invention all combinations with microbial active ingredients are claimed, in particular with antibiotics and their combinations, antiseptic substances, antimicrobial peptides and proteins, bacteriophages, salts—in particular of silver or bismuth, finest divided metallic silver, and antimicrobially acting combinations of these active ingredients with one another and other active ingredients. Claimed is also the combination with anti-proliferative, cytostatic, immunosuppressive or anti-inflammatory substances.

Especially preferred is moreover the combination with active ingredients that can affect specifically or non-specifically the bone metabolism. These include many vitamins, in particular vitamin D, moreover substances that have an inhibiting action on osteoclasts and in general on inflammation cells or inhibit specific metabolism reactions of the osteoclasts and inflammation cells such as in particular their production and secretion of acid (for example, proton pump inhibitors, bisphosphonates). In particular included are also active ingredients that stimulate a differentiation of osteoblasts from precursor cells such as the growth factors of the TGFβ family, in particular BMP 2 and BMP 7, other growth and differentiation factors as well as active ingredients that generally may increase locally the metabolism performance (such as PTH, PTH fragments, IGF, and other anabolic hormones) and those that enhance the formation of blood vessels in the implant surroundings (such as FGF or VEGF).

Many of the aforementioned active ingredients—and additional ones relevant for the bone—are not combinable in a meaningful way in prior art bone cements because they cannot withstand the polymerization conditions, may not be released or not released in a sufficient quantity, have risky long-term effects or, because the predominant part of active ingredient is not released, are not suitable for economic reasons for combining with conventional bone cement. Many of these active ingredients are combinable for the first time in combination with the polymer system according to the invention in a pharmacologically expedient way with an implant material and/or a bone cement.

The implant materials according to the invention can be produced in a simple way. The mixing step is already possible in a simple mixing cup with excellent results. In the context of a simple mixing action and reproducible quality of the mixing result, the processing of the polymer system in a pre-filled and pre-packaged container and mixing system is a particularly preferred administration form. In this connection, there is also a great advantage relative to conventional bone cements that cannot be processed in such simple mixing systems that are usually embodied as double-chamber syringes. Suitable double-chamber syringes for the polymer system according to the invention are obtainable e.g. from the company Mixpac®. The claim is however not limited to these brands but also encompasses all systems, including those that are mechanically driven and e.g. customarily employed by dentists or dental technicians and are used in this connection for mixing highly viscous pastes (e.g. for impression materials). The customary mixing ratios range from 1:1 through 1:2, 1:4 to 1:10, but can also be adjusted to other ratios. For the polymer systems according to the invention mixing ratios of 1:1, 1:2, and 1:4 are in particular suitable and preferred.

The field of bone implant materials is a preferred field of application of the implant materials according to the invention in which the principal advantages of the implant material according to the invention are particularly apparent and particularly pronounced. As already mentioned before, the conventional bone cements, despite their wide use, have severe weaknesses in some aspects that can be at least partially overcome with the polymer systems according to the invention. They will be summarized briefly in the following:

In contrast to the complex mixing of powders in conventional bone cements the pastes can be prepared in a simple way and in inexpensive machines (e.g. planetary mixer). The risk of separation of powders of different density and grain size is not present. The pastes can be mixed with one another without problem without the risk of admixture of air bubbles. No macro defects result which in conventional bone cements present a significant problem for the mechanical performance.

The shrinkage that is known from conventional bone cements and that is particularly disadvantageous occurs for the bone cements according to the present invention to a significantly reduced extent and, depending on the formulation, can be almost completely suppressed. Since in conventional bone cements the shrinkage is a function of the monomer contents and the polymer system according to the invention employs a much reduced amount of monomers, the shrinkage is in this case also significantly lower.

Like shrinkage the exothermicity is also a function of the monomer contents and accordingly it is also reduced in the same way. Moreover, in the water-based pastes the introduced water enhances with its high heat capacity as an effective means the temperature increase during polymerization to an acceptable level.

The polymer systems according to the invention in many cases do not achieve the absolute mechanical values of the conventional bone cements for compression strength and bending strength but they are in many cases (depending on the formulation) above the standard values. On the other hand, the polymer systems according to the present invention have such a mechanical behavior—and for this reason they are primarily proposed herein—that they are predestined in particular for filling spongy bone defects. In particular, their stiffness is significantly reduced so that as an implant they will damage the adjoining bone to a lesser degree. Moreover, special formulations exhibit pronounced damping properties. Surprisingly, however some of the tested formulation also have static strength values which are comparable to those of the best conventional bone cements. Applicability for fixation of joint implants is thus also provided.

The superior release of active ingredients has already been mentioned in detail.

The bioactivity is superior in the polymer systems according to the present invention with respect to several aspects. On the one hand, by the variety of combination possibilities with bioactive ingredients, secondly by the reduced hardness that enhances biomechanical induction of bone healing, thirdly by the possible introduction of bioactive minerals and combination with mineralization seeds, and fourthly by the possible realization of an interconnected pore system that enables growing in of bone and blood vessels deeply into the cement matrix.

As a result of these advantages, the use of the polymer systems according to the invention for producing bone replacement material, bone cements, bone adhesives, and implantable active ingredient carriers is particularly preferred. Bone cements are configured in accordance with the implant material of the present invention and are matched to the specific applications. Bone replacement materials are formulations based on the implant material according to the invention, for example, for filling bone defects. In this case, it can be advantageous that the bone replacement material is shaped in the form of a cured solid workpiece from the implant material according to the present invention before implantation into the body and subsequently is introduced/implanted into the bone defect.

Bone adhesives are formulations of the implant material according to the present invention, for example, for bonding and securing bone fragments after bone fractures or for attachment of, for example, metallic or ceramic or other polymer implant materials on or in the bone. In this function, the bone adhesives contain in addition to the implant material according to the invention adhesion-enhancing substances that are known from the dental field as adhesion promoters and/or substances such as polyacrylate, anionic monomers, and polymers and/or copolymers produced therefrom. These substances are used in the dental field inter alia for improvement of depletion of filler materials on the tooth substance (which is very similar to bone substance). They are combinable particularly advantageously and versatilely with the implant material according to the invention because they can be combined with the first component of the polymers system as well as with the second component of the polymer system in wide concentration ranges. This differentiates the implant materials according to the invention from conventional formulations because the charged or strongly polar adhesion promoters that in this respect are particularly effective have no or only minimal solubility in conventional bone cements (or their monomer solutions). Particular preferred is the combination with polyacrylic add, copolymers of acrylic acid and/or methacrylic acid, in particular copolymers with maleic acid and their salts. Also particularly preferred in this respect are combinations with phosphate group-containing (ethylene-unsaturated) monomers and/or polymers or copolymers produced therefrom. Especially preferred are admixtures of the aforementioned adhesion promoters in a concentration of 0.1 to 50% relative to the total weight of the implant material. The addition of adhesion promoters effects a stronger adhesion of the implant material on the bone tissue.

Active ingredient carriers are formulations of implant materials according to the invention that contain pharmacologically active ingredients in concentrations that effect a therapeutic function in the human or animal organism. These active ingredients are released from the implant material after implantation. Preferred is therefore the combination with active ingredients that develop a direct local action and thus directly act on the tissue in the surroundings of the implant material. Preferred is the combination with active ingredients that stimulate the bone metabolism and counteract local inflammations. Especially preferred are active ingredient carriers on the basis of the implant materials according to the invention that contain antimicrobial active ingredients such as antibiotics.

An especially preferred application of the polymer systems according to the invention is the filling of bone defects and the augmentation of osteoporotic bone. In the predominant number of cases this application is done by minimally invasive operation technique.

A typical example for this are the various methods of vertebroplastics which in recent years have become more and more popular and whose clinical effectiveness has been documented increasingly better. It is therefore to be assumed that these treatment techniques will be further developed and the number of treated cases will increase significantly. The further development of methods of vertebroplastics (including the so-called kyphoplastics) are particularly dependent on the availability of improved augmentation materials. The currently available bone cements are only suitable to a limited extent; even though some products are offered specifically for vertebroplastics they are still only conventional bone cements with slightly modified viscosity, curing kinetics and increased contents of x-ray contrast material. The polymer systems according to the invention are superior in principle in these applications because they are much simpler with regard to handling, exhibit reduced shrinkage, reduced heat development, higher bioactivity and improved biomechanical compatibility with the bone.

For clinically successful application they must be combined with suitable application systems for introduction of the polymer system into the bone. For this purpose, in the simplest case simple syringe systems can be employed as they are used today in connection with vertebroplastics. Expedient is however a mixing action of the polymer system in a double chamber syringe and a static mixer and the combination with an injection cannula or a suitable tube that extends to the site of implantation. Advantageous is in particular that the polymer system is mixed only upon extrusion i.e., in a simple way by means of a cement cartridge several injections can be made and no temporally matched preparation is required because the polymer system is dispensed already application-ready from the syringe.

An especially preferred application is the method known as kyphoplastics in which first the osteoporotic bone of the vertebra body is expanded by a balloon and compressed in the surroundings and subsequently a bone cement is applied into the produced cavity. Especially in this application the combination of the application instrumentation with the polymer system according to the invention is particularly advantageous because in this case an advantageous application system can be combined with an advantageous filler material. Therefore, all combinations of the polymer system according to the invention with application systems are claimed that are suitable to introduce in a minimally invasive way the polymer system according to the invention into bone defects, fracture gaps, osteoporotic bone, bone tumors or bone structures that in any other way are rarefied. Also, all attachments are claimed that can be attached to a mixing system of the type of the aforementioned double chamber syringes or can be connected with such a system for the purpose of applying with their aid the polymer system according to the invention to the target location.

The implant materials according to the invention can be handled in a particularly advantageous way intraoperatively i.e., can be prepared for the introduction into the body. This differentiates them fundamentally from conventional bone cements that are mixed from powder and liquid. At the same time, the material properties enable the simple and reliable minimally invasive application by means of a cannula. The free combinability of the first and the second components of the polymer system in a very broad mixing ratio (e.g. 1:1, 1:2, 1:4) enables also the use of the compositions according to the invention for the production of bone adhesives, bone replacement materials, and implantable active ingredient carriers in addition to the application as bone cements.

DESCRIPTION OF PREFERRED EMBODIMENTS

Based on the following examples the invention will be explained in more detail.

Example 1

Example for the principal composition of the polymer system according to the invention:
a) component 1: 30 g polymer powder Degacryl® 6658 F (copolymer of PMMA and PMA (94:6) containing 1.5% BPO, particle size approximately 45 μm); 15 ml water (demineralized); 0.45 g surface-active agent (Tween 80); 0.3 g carboxymethyl starch (type PO);
b) component 2: 10 ml methylmethacrylate (MMA) containing 0.5% DMPT.

Example 1 shows in a simple experiment the functional principle of the polymer system according to the invention. As a first component a commercially available polymer known from dental technology and supplied by the company Degussa (Degacryl® 6658 F) is used. This polymer is mixed with the aqueous solution of a surface-active agent—for improved miscibility of the polymer powder with the aqueous solution and subsequent mixture of the paste with the monomer liquid—and a polymer (carboxymethyl starch)—for increasing the viscosity—to a macroscopic homogenous paste. The thus obtained paste shows excellent storage properties in that it exhibits no noticeable changes after storage in a closed glass vessel under normal conditions for two months. The second component is comprised in this example of conventional bone cement monomer. The starter system is comprised of BPO/DMPT and is distributed, as in conventional bone cement, onto both components.

Mixing of the components 1 and 2 is realized in a mixing cup with a spatula. After a mixing duration of one minute a homogenous mixture is obtained which in approximately five minutes cures with heat development. Cylindrical shaped bodies of this mixture with dimensions of 10 mm diameter and 20 mm height achieve after incubation over night in simulated bone liquid at 37° C. a compression strength of 35-50 MPa.

The results showed that upon mixing of the water-based paste of polymer powder with a monomer liquid that are derived each of the composition of conventional bone cements, a polymerization reaction is initiated that allows the conclusion that the polymer powder suspended in water bonds with the monomer solution, that the polymer powder partially is solubilized or dissolved, that the BPO contained in the polymer powder is extracted from it and is dissolved in the monomer, that in the monomer solution by the encounter of the two starter components a polymerization reaction is initiated, and that by polymerization an intimate bonding between polymer powder and polymerized monomer is formed. The obtained solid achieves a high compression strength that is less than that of conventional bone cements but in this connection it must be taken into account that the obtained solid has a porosity of >30.% (see also example 3).

Surprisingly, the described formulation cures significantly faster than a comparable formulation of powdery Degacryl® 6658 F that is mixed with the same monomer and requires approximately 12 minutes until cured.

Example 2

Example for producing a bone cement according to the invention on the basis of Palacos (Heraeus-Kulzer)
Component 1: 40 g powder of the bone cement Palacos® R of the company Heraeus-Kulzer containing a mixture of PMMA/PMA copolymers, x-ray contrast agent (zirconium dioxide), and benzoyl peroxide (BPO) are mixed with 15 ml of an aqueous solution containing 2.5% surface-active agent (Tween® 80) and 2% carboxymethyl starch (type PO) to a paste. The paste is macroscopically homogeneous and will not separate under normal conditions.
Component 2: 10 ml methylmethacrylate (MMA) containing 0.5% DMPT.

Mixing of components 1 and 2 in a mixing cup. After short mixing duration with a spatula a homogeneous mixture is obtained that cures in approximately five minutes with heat development. Cylindrical shaped bodies of this mixture with the dimensions 10 mm diameter and 20 mm height achieve after incubation over night in simulated body liquid at 37° C. a compression strength of >50 MPa.

Example 2 shows that the results of example 1 can also be transferred onto a formulation of a commercially available conventional bone cement. Surprisingly, this formulation also cures significantly faster than comparable formulation of the powdery bone cement Palacos® that is mixed with the same monomer and requires approximately 13 minutes until cured.

Example 3

Implant material that after curing results in a solid with interconnected pore system:
 a) component 1: 30 g polymer powder Degacryl® 6658 F (copolymer of PMMA and PMA (94:6) containing 1.5% BPO, particle size approximately 45 μm); 15 ml water (demineralized); 0.45 g surface-active agent (Tween 80); 0.3 g carboxymethyl starch (type PO).
 b) component 2: 7 ml methylmethacrylate (MMA) containing 0.5% DMPT.

Mixing of components 1 and 2 is done in a mixing cup with a spatula. After a mixing duration of one minute a homogeneous mixture is obtained that cures in approximately five minutes with heat development. Cylindrical shaped bodies of this mixture with the dimensions 10 mm diameter and 20 mm height achieve after incubation over night in simulated body liquid at 37° C. a compression strength of 30-40 MPa.

Figure 1:
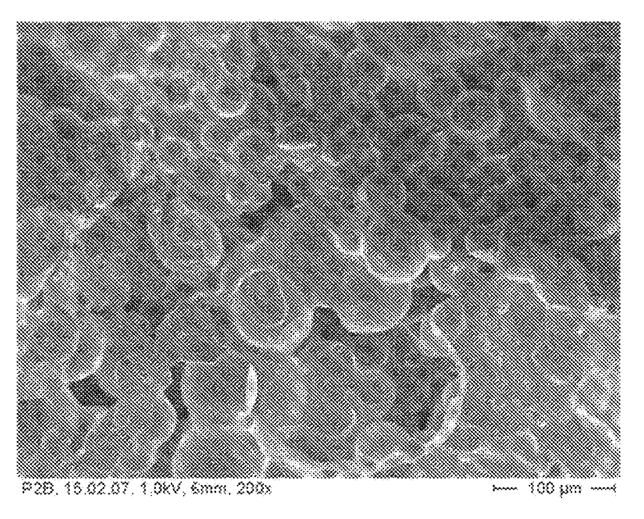
FIG. 1 shows an image made by scanning electron microscope of the product obtained according to Example 3.

Spherical shaped bodies of this mixture of 20 mm diameter after complete curing over night in simulated body liquid are dried in a drying cabinet at 37° C. and show a weight loss of approximately 35% which corresponds to the calculated porosity. After subsequent renewed incubation in simulated body liquid for 24 hours the shaped bodies absorb again the same amount of liquid. This results prove the interconnected porosity. FIG. 1 shows in this connection an image made by scanning electron microscope.

Example 4

Application Kit

The application kit is comprised of a double chamber syringe of the company Mixpac® and two components according to Example 1.

20 ml of the component 1 according to example 1 is filled into the larger chamber of a double chamber cartridge (4:1) of the company Mixpac and is closed, free of air bubbles, with a plunger. Subsequently, the smaller chamber is filled completely by means of a syringe with a monomer, in which prior to this 5% of a PMMA polymer (MW 230,000) has been dissolved homogeneously, after the plunger has been moved to the same position as in the larger chamber. The double chamber cartridge is subsequently closed off by closure plug. For the purpose of mixing and dispensing the cartridge is introduced into a dispensing device and the closure plug is removed and exchanged for a static mixer. Subsequently, the plungers of the chambers are uniformly forced by the dispensing device forwardly and the paste as well as the monomer solution are pressed through the static mixer whereby an intimate mixing is performed. The first milliliter of extruded material is disposed of as being insufficiently homogeneously mixed and the further extruded material is homogeneously mixed and cures like the manually mixed material in approximately 5 minutes. By means of the double chamber syringe the material can be applied easily.

Example 5

Implant material that after curing forms a solid with interconnected pore system as a function of selected mixing ratios of the first and second components of the polymer system and preparation in a two-chamber mixing system.
 c) component 1: 20 g polymer powder Degacryl® 6658 F (copolymer of PMMA and PMA (94:6) containing 1.5% BPO, particle size approximately 45 μm); 5 g x-ray contrast agent (zirconium dioxide); 11 ml water (demineralized) containing 2.5% surface-active agent (0.275 g Tween 80); 0.4 g polyethylene oxide (Polyox 574); 0.4 g sodium oleate; 0.5 g calcium chloride.
 d) component 2: methylmethacrylate (MMA) containing 0.5% DMPT with 20% Degacryl M546 and 2% emulsifying agent (oleic acid).

Mixing of the components 1 and 2 is done in a two chamber mixing system wherein the indicated mixing ratio represents the ratio of component 1 to component 2. Mixing and dispensing of the components in the two chamber mixing system is realized as desired by means of a dispenser or by means of a plunger by hand. By ejecting the paste material through a static mixer a homogeneous mixture is obtained that cures in approximately 5 minutes with heat development. Cylindrical shaped bodies of this mixture with dimensions of 6 mm diameter and 12 mm height achieve after incubation over night in simulated body liquid at 37° C. a compression strength of approximately 30-50 MPa, depending on the mixing ratio, respectively.

| mixing system 4:1, dispenser | mixing system 2:1, dispenser | mixing system 1:1, manual plunger |
|---|---|---|
| 10 ml double chamber cartridge, mixing attachment diameter 3.2 mm × length 16 mm compression strength: 28.92 +/− 1.24 MPa porosity: approximately 23% processing: excellent extrusion behavior complete cartridge emptying possible homogeneously mixed cement paste | 25 ml double chamber cartridge, mixing attachment diameter 4.2 mm × length 12 mm compression strength: 38.83 +/− 1.19 MPa porosity: approximately 19% processing: excellent extrusion behavior complete cartridge emptying possible homogeneously mixed cement paste | 5 ml double chamber cartridge, mixing attachment diameter 2.5 mm × length 16 mm compression strength: 48.47 +/− 1.89 MPa porosity: approximately 16% processing: excellent extrusion behavior complete cartridge emptying possible homogeneously mixed cement paste |

-continued

| mixing system 4:1, dispenser | mixing system 2:1, dispenser | mixing system 1:1, manual plunger |
|---|---|---|
| paste viscosity immediately after mixing: ● | paste viscosity immediately after mixing: ◗ | paste viscosity immediately after mixing: ○ |

Legend redescription of paste viscosity:
paste viscosity ●: high viscosity of the cement mixture, shape stability of the extruded cement mixture - bead of the cement mixture remains shape after extrusion
paste viscosity ◗: average viscosity of the cement mixture, bead current of the cement mixture runs easily, bead shape still recognizable
paste viscosity ○: minimal viscosity of the cement mixture, bead of the cement mixture runs, individual beads combine Mechanical parameters after a sample preparation in mixing cup:

| mixing ratio 4:1 | mixing ratio 2:1 | mixing ratio 1:1 |
|---|---|---|
| compression strength: 34.17 +/− 1.55 MPa | compression strength: 47.17 +/− 4.84 MPa | compression strength: 53.78 +/− 3.26 MPa |

Abbreviations:

| | |
|---|---|
| bis-GMA | bisphenol A dyglycidyl ether methacrylate (bis-GMA) |
| BMP | bone morphogenetic protein |
| BPO | di-benzoyl peroxide |
| DMPT | dimethyl-p-toluidine |
| DMSO | dimethyl sulfoxide |
| FGF | fibroblast growth factor |
| HEMA | hydroxyethyl methacrylate |
| HPMA | hydroxypropyl methacrylate |
| IGF | insulin-like growth factor |
| MMA | methylmethacrylate |
| PEG | polyethylene glycol |
| PEO | polyethylene oxide |
| PPG | polypropylene glycol |
| PVA | polyvinyl alcohol |
| PVP | polyvinyl pyrrolidone |
| PMMA | polymethylmethacrylate |
| PTH | parathyroid hormone |
| TGF | transforming growth factor |
| VEGF | vascular endothelial growth factor |

What is claimed is:

1. A two-component system for formation of an implant material on the basis of a polymer system, the two-component system comprising:
a first component and a second component that is provided separate from the first component;
wherein the first component of the polymer system is a paste that contains at least one biocompatible polymer powder and a starter component for initiating a polymerization reaction, wherein the paste comprises a carrier liquid, wherein under normal conditions the at least one biocompatible polymer powder does not dissolve or significantly swell in the carrier liquid and wherein the starter component does not dissolve in the carrier liquid and is stable in the carrier liquid; and
wherein the second component of the polymer system contains at least one reactive organic liquid or a solution or a suspension of a reactive organic liquid and of a polymer.

2. The two-component system according to claim 1, wherein the at least one biocompatible polymer is selected from homopolymers or copolymers of acrylic acid esters, methacrylic acid esters, styrene derivatives, vinyl derivatives or their mixtures.

3. The two-component system according to claim 1, wherein the carrier liquid is selected from water, aqueous solutions, glycerin, glycerin esters, propane diol, low-molecular PEG (PEG: polyethylene glycol), PEG-PPG copolymers (PPG: polypropylene glycol), DMSO (dimethyl sulfoxide), methyl pyrrolidone, biocompatible oils, or their mixtures with one another or their mixtures with one another and with other substances.

4. The two-component system according to claim 1, wherein the second component contains as a reactive organic liquid methylmethacrylate or homologue esters of methacrylic acid or their mixtures.

5. The two-component system according to claim 1, wherein the polymer of the second component is a polyacrylic acid ester or a polymethacrylic acid ester or a polystyrene or their copolymer.

6. The two-component system according to claim 1, wherein the first and second components of the polymer system contain a starter system of a two-component radical starter, comprising the starter component that is present in the first component of the polymer system and a second radical starter component with a co-starter, polymerization accelerator or initiator, wherein the starter component is present in the first component of the polymer system in undissolved form and the second radical starter component is contained in the second component of the polymer system.

7. The two-component system according to claim 6, wherein the starter component is a peroxide and the second radical starter component is a tertiary amine.

8. The two-component system according to claim 1, wherein the first component or the second or both the first and second components of the polymer system contain auxiliary agents or active ingredients or both auxiliary agents and active ingredients.

9. The two-component system according to claim 1, wherein the carrier liquid of the first component of the polymer system and the reactive organic liquid of the second component of the polymer system are immiscible with one another or not or only minimally soluble in one another and upon mixing the first and second components substantially a physical mixture results.

10. The two-component system according to claim 9, wherein at least one of the first and second components of the polymer system contains at least one biocompatible surface-active agent that assists in forming a physical mixture of the first and second components.

11. The two-component system according to claim 9, wherein at least one of the first and second components of the polymer system contains at least one biocompatible surface-active agent selected from an anionic surface-active agent and a non-ionic surface-active agent.

12. The two-component system according to claim 9, wherein at least one of the first and second components of the polymer system contains at least one biocompatible anionic surface-active agent and at least one of the first and second components of the polymer system contains a non-ionic surface-active agent or a co-surfactant.

13. The two-component system according to claim 9, wherein at least one of the carrier liquid of the first component and the reactive organic liquid of the second component of the polymer system contains water-soluble monomers or water-soluble macromers that can polymerize during or after polymerization of the polymer system within an aqueous phase of the polymer-based solid that is being formed.

14. The two-component system according to claim 13, wherein the water-soluble monomers are selected from methacrylic acid, HEMA (hydroxyethyl methacrylate), HPMA (hydroxypropyl methacrylate), HEMA phosphate, sulfopropyl methacrylate, their homologues or their mixtures.

15. The two-component system according to claim 13, wherein the water-soluble macromers are selected from PEG-mono-methacrylate (PEG: polyethylene glycol), PEG-di-methacrylate, branched PEG-n-methacrylates, their homologues or their mixtures.

16. The two-component system according to claim 1, wherein the first and second components of the polymer system contain dissolved polymers or finely divided suspended organic, inorganic or organo-mineral components for adjusting a viscosity of the first and second components of the polymer system, wherein the viscosity of the first and second components of the polymer system does not surpass the value of 200 Pa*s.

17. The two-component system according to claim 1, wherein at least one of the first and second components of the polymer system contains microcrystalline, nanocrystalline or amorphous bone minerals or synthetic bone-analog minerals.

18. The two-component system according to claim 1, wherein at least one of the first and second components of the polymer system contains at least one biocompatible substance that serves as a crystallization seed for mineral depositions, enhances the formation of mineral depositions, or serves as a crystallization seed for mineral depositions and enhances the formation of mineral depositions, wherein the at least one biocompatible substance contains at least one carboxyl, sulfate, and/or phosphate group and/or a siloxane group.

19. The two-component system according to claim 1 for producing bone cements, bone replacement materials, bone adhesives, and implantable active ingredient carriers.

20. An application kit comprising:
a two-component system according to claim 1;
a double chamber syringe and a forced mixer/static mixer or components connectable to form a double chamber syringe and combinable with a forced mixer/static mixer.

21. A combination of a two-component system according to claim 1 and an of application system for use in augmentation of osteoporotic or other pathologically changed bone areas and for use in filling bone defects of any kind.

* * * * *